(12) United States Patent
Brandeis

(10) Patent No.: US 10,265,470 B2
(45) Date of Patent: Apr. 23, 2019

(54) DEVICE FOR SYNCHRONIZED INJECTION AND ASPIRATION

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 356 days.

(21) Appl. No.: 15/028,968

(22) PCT Filed: Oct. 1, 2014

(86) PCT No.: PCT/IL2014/050864
§ 371 (c)(1),
(2) Date: Apr. 13, 2016

(87) PCT Pub. No.: WO2015/052704
PCT Pub. Date: Apr. 16, 2015

(65) Prior Publication Data
US 2016/0263319 A1  Sep. 15, 2016

Related U.S. Application Data

(60) Provisional application No. 61/890,270, filed on Oct. 13, 2013.

(51) Int. Cl.
*A61M 5/19* (2006.01)
*A61B 17/00* (2006.01)
(Continued)

(52) U.S. Cl.
CPC .......... *A61M 5/19* (2013.01); *A61B 17/00008* (2013.01); *A61M 1/007* (2014.02);
(Continued)

(58) Field of Classification Search
CPC ............ A61M 1/0058; A61M 5/14216; A61M 5/14566; A61M 5/19; A61M 5/31511;
(Continued)

(56) References Cited

U.S. PATENT DOCUMENTS 5,492,535 A * 2/1996 Reed .................... A61M 1/1081
417/437
5,868,708 A   2/1999 Hart et al.
(Continued)

FOREIGN PATENT DOCUMENTS

DE      3328530      2/1985
GB      526145       9/1940
(Continued)

OTHER PUBLICATIONS

Restriction Official Action dated Jan. 29, 2018 From the US Patent and Trademark Office Re. U.S. Appl. No. 15/028,965. (8 pages).
(Continued)

*Primary Examiner* — Brandy S Lee

(57) ABSTRACT

There is provided a device for automatic synchronized injection and aspiration of fluids comprising: a first linear actuator; a second linear actuator; a first coupling mechanism attached at a distal end portion of the first linear actuator, the first coupling mechanism arranged for detachable coupling to a first plunger of a first syringe; a second coupling mechanism attached at a distal end portion of the second linear actuator, the second coupling mechanism arranged for detachable coupling to a second plunger of a second syringe; and a synchronization mechanism mechanically coupled to the first and second linear actuators, the mechanism arranged so that insertion of the first plunger further into a first barrel of the first syringe is synchronized with extraction of the second plunger from a second barrel of the second syringe, thereby injection from the first syringe is synchronized with aspiration into the second syringe.

20 Claims, 8 Drawing Sheets

(51) Int. Cl.
- *A61M 5/145* (2006.01)
- *A61M 5/315* (2006.01)
- *A61M 5/142* (2006.01)
- *A61M 1/00* (2006.01)
- *A61M 5/178* (2006.01)

(52) U.S. Cl.
CPC ........ *A61M 1/0009* (2013.01); *A61M 1/0058* (2013.01); *A61M 5/14216* (2013.01); *A61M 5/14566* (2013.01); *A61M 5/31511* (2013.01); *A61B 2217/005* (2013.01); *A61M 2005/1787* (2013.01)

(58) Field of Classification Search
CPC ................ A61M 1/0009; A61M 1/007; A61M 2005/1787; A61B 17/00008; A61B 2217/005
See application file for complete search history.

(56) References Cited

U.S. PATENT DOCUMENTS

| | | |
|---|---|---|
| 6,962,576 B2 | 11/2005 | Sibbitt |
| 8,177,740 B1 | 5/2012 | McGlothlin et al. |
| 2001/0009989 A1 | 7/2001 | Sibbitt |
| 2002/0010418 A1 | 1/2002 | Lary et al. |
| 2002/0010487 A1 | 1/2002 | Evans et al. |
| 2003/0069549 A1 | 4/2003 | MacMahon et al. |
| 2003/0097114 A1 | 5/2003 | Ouriel et al. |
| 2004/0004521 A1 | 1/2004 | Hasegawa |
| 2006/0184130 A1 | 8/2006 | Sibbitt, Jr. et al. |
| 2007/0244429 A1 | 10/2007 | Nguyen et al. |
| 2010/0042117 A1 | 2/2010 | Kim et al. |
| 2011/0152683 A1 | 6/2011 | Gerrans et al. |
| 2012/0090620 A1 | 4/2012 | Deutsch |
| 2013/0261538 A1 | 10/2013 | Miyazaki et al. |
| 2016/0242790 A1 | 8/2016 | Brandeis |
| 2016/0250143 A1 | 9/2016 | Brandeis |

FOREIGN PATENT DOCUMENTS

| | | |
|---|---|---|
| WO | WO 2004/112569 | 12/2004 |
| WO | WO 2007/114934 | 10/2007 |
| WO | WO 2009/104189 | 8/2009 |
| WO | WO 2009/109967 | 9/2009 |
| WO | WO 2009/120432 | 10/2009 |
| WO | WO 2015/052702 | 4/2015 |
| WO | WO 2015/052703 | 4/2015 |
| WO | WO 2015/052704 | 4/2015 |

OTHER PUBLICATIONS

Invitation Pursuant to Rule 137(4) EPC and Article 94(3) EPC dated Jun. 16, 2017 From the European Patent Office Re. Application No. 14803252.7. (1 Page).
Communication Pursuant to Article 94(3) EPC dated Jan. 31, 2018 From the European Patent Office Re. Application No. 14803252.7. (4 Pages).
Official Action dated Apr. 13, 2018 From the US Patent and Trademark Office Re. U.S. Appl. No. 15/028,965. (16 pages).
Communication Relating to the Results of the Partial International Search dated Feb. 4, 2015 From the International Searching Authority Re. Application No. PCT/IL2014/050863.
International Preliminary Report on Patentability dated Apr. 28, 2016 From the International Bureau of WIPO Re. Application No. PCT/IL2014/050862.
International Preliminary Report on Patentability dated Apr. 28, 2016 From the International Bureau of WIPO Re. Application No. PCT/IL2014/050863.
International Preliminary Report on Patentability dated Apr. 28, 2016 From the International Bureau of WIPO Re. Application No. PCT/IL2014/050864.
International Search Report and the Written Opinion dated Feb. 10, 2015 From the International Searching Authority Re. Application No. PCT/IL2014/050862.
International Search Report and the Written Opinion dated Feb. 23, 2015 From the International Searching Authority Re. Application No. PCT/IL2014/050863.
International Search Report and the Written Opinion dated Feb. 23, 2015 From the International Searching Authority Re. Application No. PCT/IL2014/050864.
Eckmann "Polidocanol for Endavenous Microfoam Sclerosant Therapy", Expert Opinion on Investigational Drugs, 18(2): 1919-1927, Dec. 2009.
Elias et al. "Mechanochemical Tumescentless Endovenous Ablation: Final Results of the Initial Clincal Trial", Phlebology, 27: 67-72, 2012.
Jones et al. "Management of Varicose Veins", American Family Physicians, 78(11): 1289-1294, 2008.
Subramonia et al. "The Treatment of Varicose Veins", Annals of The Royal College of Surgeons of England, 89(2): 96-100, Mar. 2007.

\* cited by examiner

DEVICE FOR SYNCHRONIZED INJECTION AND ASPIRATION

The present application is a National Phase of PCT Patent Application No. PCT/IL2014/050864 having International filing date of Oct. 1, 2014, which claims the benefit of priority under 35 USC § 119(e) of U.S. Provisional Patent Application No. 61/890,270 filed on Oct. 13, 2013. The contents of the above applications are all incorporated by reference as if fully set forth herein in their entirety.

RELATED APPLICATIONS

PCT Patent Application No. PCT/IL2014/050864 is related to co-filed, co-pending and co-assigned PCT Patent Application Nos. PCT/IL2014/050862 and PCT/IL2014/050863, both by the same inventor, Zeev Brandeis. PCT Patent Application No. PCT/IL2014/050862 describes a foam formation device for forming foam suitable for intra-body medical treatment. PCT Patent Application No. PCT/IL2014/050863 describes a device and/or method for vein ablation by irritation. The contents of the above applications are all incorporated by reference as if fully set forth herein in their entirety.

FIELD AND BACKGROUND OF THE PRESENT INVENTION

The present invention, in some embodiments thereof, relates to a device for synchronized injection and aspiration and, more particularly, but not exclusively, to a device for synchronized injection and aspiration using syringes.

Some medical procedures involve injection of fluid into the patient, and removal of fluid from the patient. For example, treatment of an abscess may be performed by draining pus from the body cavity, and injection of saline into the cavity. The saline may be used to flush out remaining pus and other debris from the cavity. The injection and removal may be performed sequentially and iteratively by the healthcare provider, until all the pus has been removed and the cavity has been cleansed.

In another example, vein ablation (e.g., of a varicose vein) may be performed by injection of a sclerosing agent into the vein, and removal of the excess sclerosant agent from the vein. The injection and aspiration may be performed in a controlled manner to help prevent spread of the agent into the rest of the vasculature. International Patent Application Publication No. WO 2009/104189, titled "METHOD AND DEVICE FOR LIQUID MEDICAL SUBSTANCE VENOUS ADMINISTRATION", by the same inventor of the present application, is an example of such a device and/or method.

Devices have been developed in order to make it easier for the healthcare provider to perform the injection and aspiration.

For example, Sibbitt, in U.S. Pat. No. 6,962,576, discloses "a reciprocating member which moves along a track parallel to the axial direction of the first syringe; and a reciprocating device connecting the first syringe plunger to the reciprocating member so that when one member of the group consisting of the first syringe plunger and the reciprocating member moves distally, the other member of the group is forced to move proximally." In summary, Sibbitt teaches "a syringe that permits both injection and aspiration with one hand".

Additional background art includes:
International Patent Application Publication No. WO 2009/109967 by the same inventor as the present application.

SUMMARY OF THE PRESENT INVENTION

An aspect of some embodiments of the present invention relates to a device for synchronized injection and aspiration between syringes, the syringes being independently attachable to and detachable from the device.

According to an aspect of some embodiments of the present invention there is provided a device for automatic synchronized injection and aspiration of fluids comprising: a first linear actuator; a second linear actuator; a first coupling mechanism attached at a distal end portion of the first linear actuator, the first coupling mechanism arranged for detachable coupling to a first plunger of a first syringe; a second coupling mechanism attached at a distal end portion of the second linear actuator, the second coupling mechanism arranged for detachable coupling to a second plunger of a second syringe; and a synchronization mechanism mechanically coupled to the first and second linear actuators, the mechanism arranged so that insertion of the first plunger further into a first barrel of the first syringe is synchronized with extraction of the second plunger from a second barrel of the second syringe, thereby injection from the first syringe is synchronized with aspiration into the second syringe.

According to some embodiments of the invention, the synchronization mechanism includes a disengaging mechanism arranged for disengaging one of the linear actuators from the synchronization mechanism when a plunger coupled to the linear actuator is pulled out of a corresponding barrel.

According to some embodiments of the invention, the first linear actuator is coupled to a first gear of the synchronization mechanism, the first gear being mounted on a track substantially parallel to a direction of movement of the first linear actuator, so that proximal displacement of the first linear actuator disengages the first gear from the rest of the synchronization mechanism and distal displacement of the first linear actuator re-engages the first gear with the rest of the synchronization mechanism.

According to some embodiments of the invention, the synchronization mechanism has 3 gearwheels which synchronize opposite movements of the first and second linear actuators.

According to some embodiments of the invention, the synchronization mechanism has a rigid and flexible rod with a curve, one end of the rod being coupled to the first linear actuator and the other end of the rod being coupled to the second linear actuator so that opposite movements of the first and second linear actuator are synchronized.

According to some embodiments of the invention, the synchronization mechanism has a wire winding around one or more pulley, one end of the wire being coupled to the first linear actuator, the other end of the wire being coupled to the second linear actuator, so that opposite movements of the first and second linear actuator are synchronized.

According to some embodiments of the invention, the first and second linear actuators have teeth, and the synchronization mechanism comprises a plurality of meshed gears, wherein at least a first gear is meshed with the teeth of the first linear actuator and at least a second other gear is meshed with teeth of the second linear actuator.

According to some embodiments of the invention, the synchronization mechanism is arranged so that distal displacement of the first linear actuator by a first distance is synchronized with proximal distal displacement of the second linear actuator by a second distance substantially different than the first distance. Optionally, the ratio between the second and the first distance corresponds to equal volume changes in the first and second syringes, wherein the volume capacity of the first and second syringes are different.

According to some embodiments of the invention, the device further comprises a base, the synchronization mechanism being mechanically attached to the base, the base comprising barrel attachment elements for reversibly coupling the barrels of the syringes to the base in a stable and substantially motion-less manner.

According to some embodiments of the invention, the first and second syringes are off-the-shelf disposable syringes.

According to some embodiments of the invention, the first and second syringes are of different volume capacities.

According to some embodiments of the invention, the first and second linear actuators are racks.

According to some embodiments of the invention, the device further comprises a guidewire having a proximal end portion coupled to the synchronization mechanism so that the guidewire is displaced one or both of distally and proximally during distal displacement of the first linear actuator. Optionally, a distal end portion of the guidewire comprises an irritation element sized and arranged to contact at least a portion of an internal wall of a vessel or cavity so that the displacement of the guidewire irritates the internal wall of the vessel or cavity. Optionally, the guidewire is coupled to the synchronization mechanism so that the guidewire is proximally retracted during injection. Optionally, the guidewire is attached to an outer perimeter portion of a gear of the synchronization mechanism so that the guidewire is wound around an axle of the gear during injection, thereby retracting the guidewire.

Optionally, the device further comprises a channel for at least partially surrounding a portion of the guidewire, the guidewire arranged with one or more features at the portion so that displacement of the guidewire portion through the channel one or both of rotate and laterally displaces the guidewire. Optionally, the internal surface of the channel comprise one or more surface features so that passage of the guidewire portion features through the channel one or both of rotate and laterally displace the guidewire.

According to some embodiments of the invention, the device further comprising a foldable handle sized for being gripped by one hand.

According to some embodiments of the invention, the device further comprises a ratchet arranged to prevent distal displacement of the second linear actuator, so that contents of the second syringe are not injected.

According to some embodiments of the invention, the first and second coupling mechanisms are arranged for independent attachment and detachment of the first and second syringes.

According to some embodiments of the invention, the device is sized to be held in one hand.

According to some embodiments of the invention, the device is located on a base which is remote from a patient, and a needle in the patient is connected via tubes to the syringes.

According to an aspect of some embodiments of the present invention there is provided a method of synchronized injection and aspiration of fluids comprising: selecting a first syringe suitable for injection of a first fluid; selecting a second syringe suitable for aspiration of a second fluid; detachably attaching the first and second syringes to a synchronization mechanism; synchronizing distal displacement of a first plunger of the first syringe with proximal displacement of a second plunger of the second syringe using a mechanical synchronization arrangement so that injection by the distal displacement and aspiration by the proximal displacement occur simultaneously; and replacing the first or second syringe with a third syringe, wherein the replacing is performed independently of the other syringe.

According to some embodiments of the invention, the first syringe is loaded by proximal displacement of the first plunger without the synchronized motion of the second plunger.

According to some embodiments of the invention, the replacing occurs during an invasive medical procedure.

According to some embodiments of the invention, the method further comprises placing the first and second syringes in fluid communication with a body chamber or vessel of a patient during a medical procedure. Optionally, the body chamber or vessel is selected from the group comprising: a vein, an abscess, a joint. Optionally, pressure within the body chamber or vessel is maintained during the distal displacement and synchronization. Optionally, the rate of fluid injection and aspiration are substantially the same. Optionally, the first and second syringes have different volume capacities. Optionally, the method further comprises irritating an internal wall of a vein during the distal displacement and synchronization. Optionally, irritating comprises scratching the inner wall by at least one of axial displacement, rotational displacement, and lateral displacement. Optionally, the replacing is performed while a needle in fluid communication with the first syringe remains in the patient.

Unless otherwise defined, all technical and/or scientific terms used herein have the same meaning as commonly understood by one of ordinary skill in the art to which the present invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings and/or images. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings.

DESCRIPTION OF SPECIFIC EMBODIMENTS OF THE PRESENT INVENTION

Figure 1:
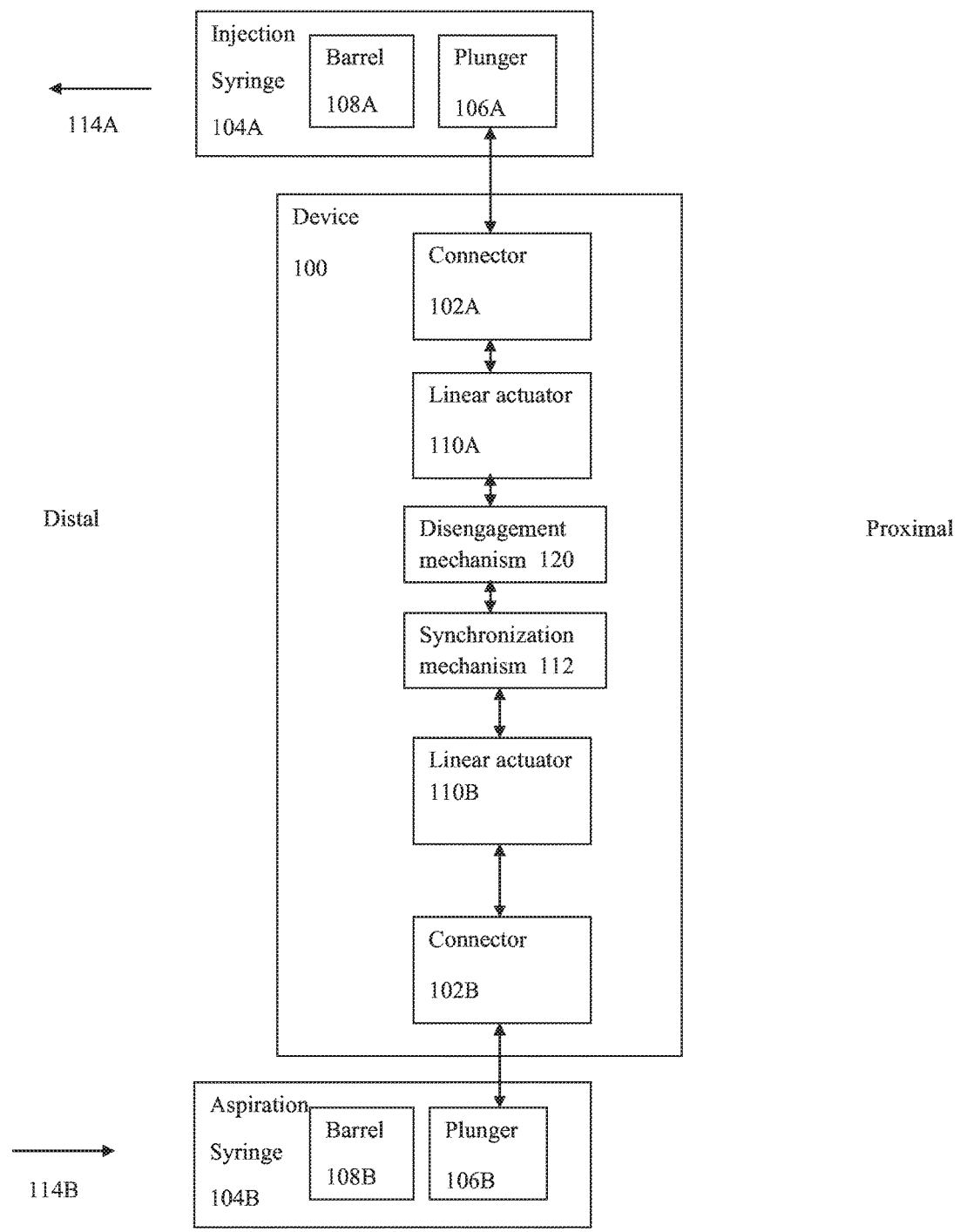
FIG. 1 is a block diagram of a syringe synchronization device, in accordance with exemplary embodiments of the present invention.

An aspect of some embodiments of the present invention relates to a synchronization device for synchronizing between injection and aspiration actions of syringes. Optionally, the syringes are off-the shelf. Optionally, the syringes are independently attachable to and detachable from the device.

Optionally, the first syringe is removed and replaced with a third syringe (or with the same first syringe) without removal or modification of the position of the second syringe. Optionally, the first syringe is replaced while the needle and/or catheter remains within the patient. Alternatively or additionally, the second syringe is removed and replaced with a fourth syringe (or with the same second syringe) without removal or modification of the position of the first syringe (or third syringe). Advantageously, one syringe may be replaced during a medical procedure without disturbing the other syringe. Advantageously, syringes may be used without tampering with sterility of the syringes and/or without modification to the syringes. Advantageously, a single device may be used multiple times with different syringes and/or in different procedures. Advantageously, sterility may be maintained within the fluids and/or syringes even if the device is not sterile. Advantageously, the device may be cost effective, as the device itself is reusable, and the syringes are low cost off-the-shelf syringes. Advantageously, the device may make it easier to perform simultaneous injection and aspiration, as both movements may be performed using only one hand, instead of, for example, two operators, or one operator using both hands.

In exemplary embodiments, the injection and aspiration are performed simultaneously.

Optionally, the device is a handheld device sized and/or shaped to fit within the palm of one hand. Advantageously, simultaneous synchronized injection and aspiration may be performed single handedly. Alternatively, the device is located on a base which is remote from a patient, and the needle in the patient is connected via tubes to the syringes. Optionally, the device is a standalone device (i.e., not handheld), and/or integrated into another device. Optionally, the device is computer controlled. For example, the device is set to automatically inject and aspirate into a patient using a timer and/or at a pre-selected rate.

Optionally, the syringes are off-the-shelf. Optionally, the syringes are single-use and disposable. For example, plastic disposable single use syringes commonly found in healthcare settings.

In exemplary embodiments, a synchronization mechanism is structured and arranged to automatically translate a movement direction of the plunger of the first syringe (i.e., injection) into an opposite movement direction of the plunger of the second syringe (i.e., aspiration). Optionally, the opposite movements are parallel. Optionally, the mechanism is arranged so that insertion of the first plunger further into the barrel of the first syringe is synchronized with extraction of the second plunger from the second barrel of the second syringe, thereby synchronizing from the first syringe is synchronized with aspiration into the second syringe. Advantageously, by pressing the plunger of the first syringe to inject, the second syringe automatically and simultaneously aspirates.

Optionally, a disengagement mechanism facilitates independent movement of one of the plungers in relation to the other plunger. Optionally, the disengaging mechanism is arranged for disengaging one of the linear actuators from the synchronization mechanism when the plunger connected to the linear actuator is pulled out of the barrel of the syringe.

As used herein, the term distally means away from the operator of the device. As used herein, the term proximally means towards the operator of the device. Optionally, the first syringe is connected to the synchronization mechanism by a displaceable gear, so that proximal displacement of the plunger of the first syringe (i.e., to fill the first syringe with fluid) disengages the gear from the synchronization mechanism, and distal displacement of the first syringe plunger (i.e., to inject) re-engages the gear with the synchronization mechanism. Advantageously, the first syringe may be filled while attached to the device, without causing injection or aspiration of the second syringe.

Optionally, the device comprises a one-way mechanism arranged for preventing distal displacement of the second syringe (i.e., injection by the aspiration syringe). For example, the mechanism is a ratchet. Optionally, the ratchet is coupled to the synchronization mechanism, for example, preventing reverse motion of one or more gears, moving wires or other structures. Advantageously, unsafe maneuvers are prevented or reduced by the ratchet, for example, injection of aspirated waste contents back into the patient.

An aspect of some embodiments of the present invention relates to a device for synchronized vessel and/or cavity irritation, injection and aspiration. In exemplary embodiments, a proximal end portion of a guidewire is connected to a synchronization mechanism that synchronizes injection from a first syringe with aspiration from a second syringe. Optionally, an irritation element is attached to the distal portion of the guidewire. During use of the device, the guidewire and irritation element are moved. Optionally, the movement of the irritation element occurs inside a body vessel, so that the inner wall of the vessel is irritated by the motion. Advantageously, a vein may be irritated by the device during simultaneous injection of a sclerosing agent and aspiration of excess sclerosant and/or other waste. The simultaneous irritation may improve the effect of the sclerosing agent on the vessel wall.

In exemplary embodiments, the device is arranged to produce pre-selected motion of the guidewire, for example, one or more of: proximal displacement, distal displacement, lateral displacement, rotational motion. Examples of possible combinations include: proximal displacement, proximal displacement with simultaneous rotational motion, proximal displacement with simultaneous lateral motion (in a radial direction), simultaneous rotational and/or lateral motion without proximal and/or distal displacement.

Optionally, the vein is mechanically irritated by the motion of the irritation element against the inner vein wall. Advantageously, the mechanical irritation may be used to improve drug delivered by the injection syringe, as irritation of the tissue may increase absorption of the drug inside the lumen. For example, irritation of the intima tissue layer of a vein may increase absorption of a sclerosant agent in the lumen of the vein to ablate the vein.

Optionally, the guidewire is coupled to the stationary part of the synchronization mechanism so that upon disengagement of the displaceable gear (e.g., during filling of the injection syringe), the guidewire is not moved during the filling of the injection syringe. Advantageously, undesired movement of the guidewire is prevented during filling of the injection syringe.

Optionally, the guidewire is coupled to the synchronization mechanism so that during injection of the first syringe, the guidewire is proximally retracted. For example, the guidewire is coupled an outer perimeter region of a surface of a relatively large gearwheel. When the gearwheel turns during injection (e.g., counter-clockwise), the guidewire attached to the proximally moving parts of the gearwheel is proximally retracted. Advantageously, proximal motion of the irritation element helps to ablate the vein as the guidewire is being retracted inside the vein.

Before explaining at least one embodiment of the present invention in detail, it is to be understood that the present invention is not necessarily limited in its application to the details of construction and the arrangement of the components and/or methods set forth in the following description and/or illustrated in the drawings and/or the Examples. The present invention is capable of other embodiments or of being practiced or carried out in various ways.

Referring now to the drawings, FIG. 1 illustrates a block diagram of a device for synchronized injection and aspiration 100, according to exemplary embodiments of the present invention. FIG. 1 provides an overall understanding of the device. Some examples of designs will be presented, for example, with reference to FIG. 2, FIGS. 3A-B, and FIGS. 7A-B. Advantageously, device 100 may be used with standard off-the-shelf syringes to inject and aspirate in a synchronized manner.

For reference, movement towards the left side of device 100 is referred to as a distal direction and movement towards the right side of device 100 is referred to as a proximal direction. Exemplary directions of fluid flow relative to device 100 are illustrated by arrows 114A-B.

In exemplary embodiments, device 100 has connectors 102A-B for detachable mechanical coupling to syringes 104A-B. Optionally, connectors 102A-B are attachable and detachable from syringes 104A-B so that syringes 104A-B are removable and/or replaceable. Suitable connectors 102A-B include, for example, clamps, rings, elastics, crimpers, casings, or other suitable structures. Optionally, connectors 102A-B are designed to attach to the end portion of plungers 106A-B of syringes 104A-B. In such a configuration, barrels 108A-B of syringes 104A-B are maintained stationary relative to device 100 (e.g., by another connector not shown in this figure), and plungers 106A-B are displaced. Optionally, connectors 102A-B are designed for attachment to syringes of different sizes.

Optionally, device 100 is attachable to syringes 104A-B of different volumes and/or sizes. Optionally, syringes 104A and 104B are of different volumes. The volume capacity of each syringe is, for example, about 1 milliliter (mL), or about 5 mL, or about 10 mL, or about 20 mL, or about 30 mL, or about 50 mL, or about 60 mL, or about 100 mL, or about 200 mL, or about 500 mL, or about 1000 mL, or other smaller, intermediate or larger volumes. Alternatively, device 100 is attachable only to syringes of a predetermined volume capacity.

In exemplary embodiments, connectors 102A-B are mechanically coupled to linear actuators 110A-B. Actuators 110A-B are designed for substantial linear displacement parallel to the direction of motion of plungers 106A-B, which is substantially along the long axis of syringes 104A-B. As used herein, the phrase substantially linear displacement means displacement in a direction so that plungers 106A-B do not get stuck within barrels 108A-B. Actuators 110A-B are, for example, rack and pinion, screw with traveling nut, or other types of linear actuators.

In exemplary embodiments, the linear motion of actuators 110A-B is synchronized by a synchronization mechanism 112. Optionally, motion of one actuator in a first direction is translated by mechanism 112 into motion in an opposite direction by the other actuator. In other words, injection by one syringe is translated into aspiration by the other syringe. Alternatively, aspiration by one syringe is translated into aspiration by the other syringe.

Alternatively, some types of motion by one actuator are not translated into corresponding motion of the other actuator by mechanism 112. Optionally, proximal displacement of plunger 106A of injection syringe 104A is not synchronized with motion of syringe 104B. That is, aspiration into injection syringe 104A does not cause injection from aspiration syringe 104B. Additional details are provided below with reference to FIGS. 3A-B. Optionally, distal displacement of plunger 106B of aspiration is prevented. For example, mechanism 112 may provide structures to only allow one way motion, for example, ratchets. Advantageously, potentially dangerous situations and/or contamination of sterile environments are prevented or reduced, for example, injection of aspirated contents back into the patient and/or aspiration of contaminants into the sterile contents of the injection syringe.

Displacement of plunger 106A may be provided, for example, manually by a thumb of the healthcare provider, automatically by a machine with a controller lever, or other controlled forces.

Synchronization mechanism 112 is constructed from any suitably designed and arranged mechanical and/or electrical components, for example, gears such as gearwheels, rack and pinion, chains, pulleys, levers, motors, or other components. Detailed examples are provided, for example, with reference to FIGS. 2, 7A and 7B.

Optionally, the synchronization mechanism is arranged so that the distal displacement distance of the first plunger and the proximal displacement distance of the second plunger are substantially equal, for example, within about 1%, or about 5%, or about 10%. Alternatively, the synchronization mechanism is arranged so that the distal and proximal displacement distances by actuators 110A-B are not of equal displacement length. For example, injecting by distal displacement of plunger 106A by about 1 centimeter (cm) is translated into a synchronized aspiration by proximal displacement of plunger 106B by about 2 cm. The ratio between distal and proximal displacement, for example, about 1.5:1, or about 2:1, or about 3:1, or about 4:1, or about 5:1, or about 10:1, or about 0.5:1, or about 0.3:1, or about 0.25:1, or about 0.2:1, or about 0.1:1, or other smaller, intermediate or larger ratios.

Alternatively or additionally, the synchronization mechanism is arranged so that distal displacement of the first syringe is synchronized with proximal displacement of the second syringe so that the volume reduction of the first syringe is synchronized with the volume increase in the second syringe. For example, the first syringe has a total 10 mL capacity and the second syringe has a total 60 mL capacity. Injecting 1 mL is synchronized with aspirating 1 mL by synchronizing the distal displacement distances of the first plunger with a smaller displacement distance of the second plunger.

Optionally, a disengagement mechanism 120 facilitates independent movement of one of the plungers in relation to the other plunger. Disengagement mechanism 120 is coupled to linear actuator 110A. Mechanism 120 is arranged to engage and disengage from synchronization mechanism 112 upon movement of actuator 110A. For example, reverse movement of actuator 110A (e.g., during loading of syringe 104A) disengages mechanism 112 from mechanism 120. Forward movement of actuator 110A (e.g., during injection) engages mechanism 112 with mechanism 120. Additional details of the disengagement mechanism are described hereinabove, for example, with reference to FIGS. 3A-B.

Figure 2:
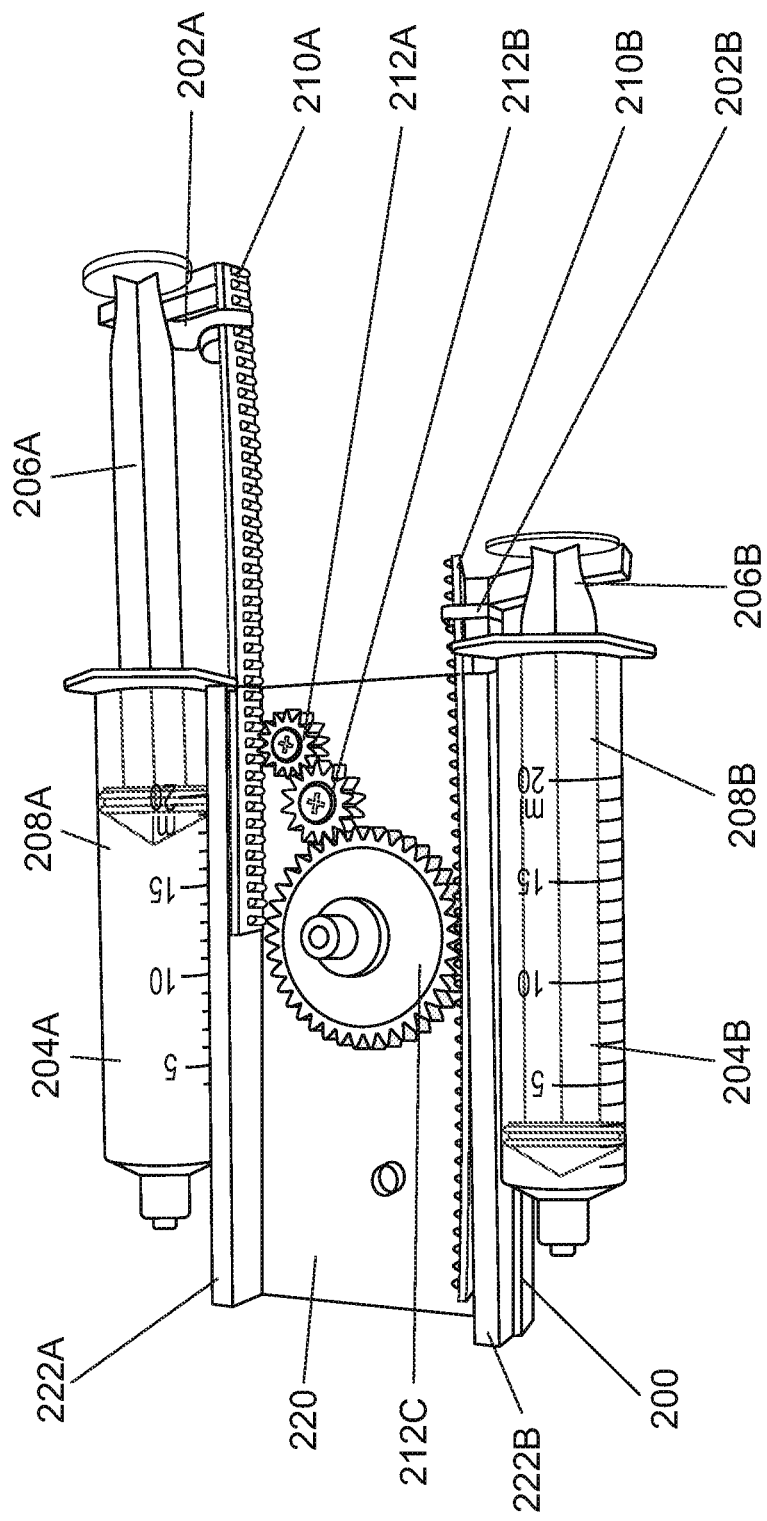
FIG. 2 is an image of an exemplary design of the syringe synchronization device, in accordance with exemplary embodiments of the present invention.

Reference is now made to FIG. 2, which is an image of an exemplary design 200 of the synchronization device 100 of FIG. 1, according to exemplary embodiments of the present invention. Device design 200 is shown in a ready to use state (before connection to external tubing), with syringe 204A ready for injection and syringe 204B ready for aspiration.

Connectors 202A-B mechanically grip plungers 206A-B of syringes 204A-B for attachment to a distal end portion of racks 210A-B. Connectors 202A-B are U-shaped clips, sized so that plungers 206A-B are secured by a click, and removable by application of a light force.

Gearwheels 212A-C act as the synchronization mechanism. Gearwheel 212A and rack 210A are meshed in a rack-and-pinion formation. Linear displacement of rack 210A rotates gearwheel 212A. Gearwheel 212A is meshed with gearwheel 212B so that gearwheel 212B rotates in an opposite direction to gearwheel 212A. Gearwheel 212C is meshed with gearwheel 212B, so that gearwheel 212C rotates in a direction opposite to gearwheel 212B, but in the same direction as gearwheel 212A. Gearwheel 212C and rack 210B are meshed in a rack-and-pinion formation so that rotation of gearwheel 212C linearly displaces rack 210B in a direction opposite to the linear displacement of rack 210A. Direction of motion during use are illustrated by the arrows on the image.

Optionally, gearwheels 212A-C are mechanically coupled to a base 220 so that gearwheels 212A-C are able to freely rotate. For example, base 220 is made from plastic, metal, or other types of materials. Optionally, the material is selected so that device 100 may be sterilized without being damaged. For example, gearwheels 212A-C are attached using suitable bearings.

Optionally, base 220 comprises elevated parallel rails 222A-B. Optionally, rails 222A-B are sized and arranged to help maintain displacement of racks 210A-B in a substantially linear direction and parallel to the long axis of syringes 204A-B. Optionally, rails 222A-B are sized and arranged to maintain the position of syringes 204A-B, for example, parallel to racks 210A-B. For example, the syringe is disposed on one side of the rail, and the rack is displaced along the opposite side of the rail.

Movements of plungers 206A-B may cause displacement of barrels 208A-B, which may reduce the volume of fluid injection and/or aspirated. Optionally, barrels 208A-B are stationary retained against based 220, for example, by a connector (not shown). Alternatively or additionally, the barrels are stabilized by a hand of the user.

Figure 3A:
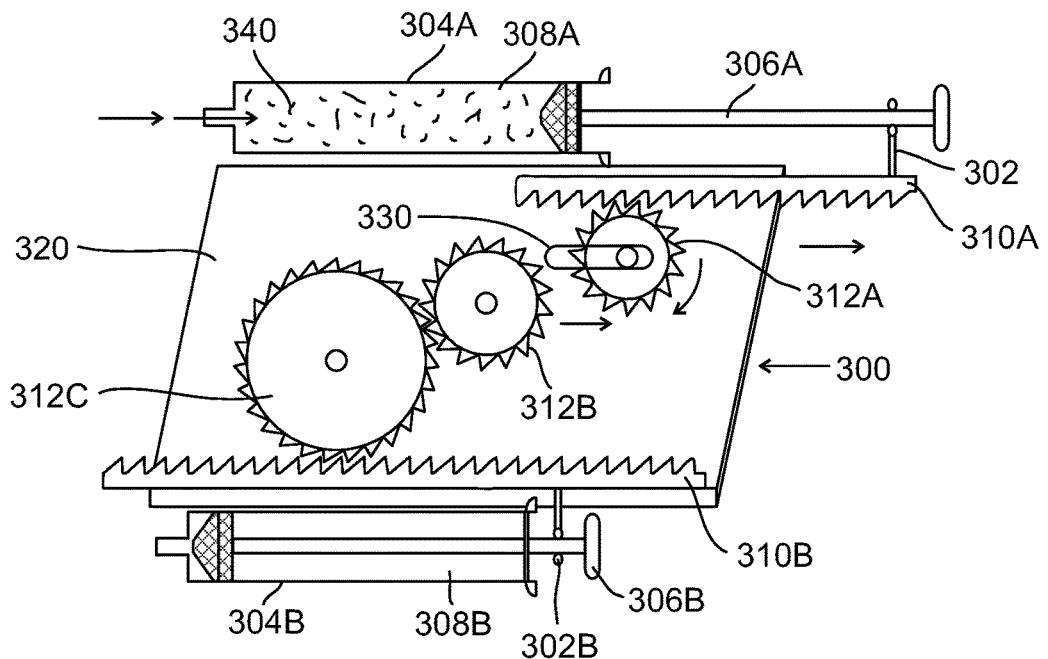
FIGS. 3A-B are schematic illustrations of an exemplary disengagement mechanism of the syringe synchronization device, in accordance with exemplary embodiments of the present invention.
Figure 3B:
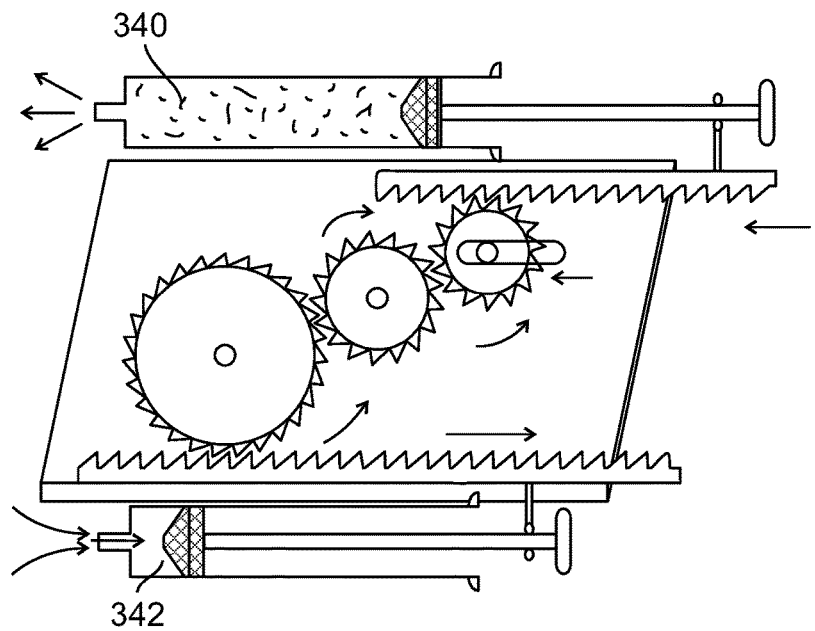

Reference is now made to FIGS. 3A-B, which are schematic diagrams of a device 300 that provides for aspiration into an injection syringe without synchronized motion of the aspiration syringe, in accordance with exemplary embodiments of the invention. FIGS. 3A-B illustrate steps during use.

Device 300 corresponds to device 200 of FIG. 2, with the added feature of a gearwheel 312A (corresponding to gearwheel 212A of FIG. 2) being coupled to a track 330 on a base 320. Track 330 is arranged so that gearwheel 312A is displaceable proximally and distally in a direction substantially parallel to the displacement direction of a rack 310A. For example, track 330 is an elongated hole in base 320 with curved endings. Gearwheel 312A is mounted within track 330 to allow rotational motional of gearwheel 312A at any position along track 330, for example, by a slideable bearing.

When located distally along track 330, the teeth of gearwheel 312A are meshed with the teeth of gearwheel 312B. Motion of gearwheels 312A and 312B are synchronized.

FIG. 3A illustrates proximal displacement of plunger 306A of injection syringe 304A, for example, to load syringe 304A with a fluid 340 for injection into the patient (direction of loading fluid 340 illustrated by arrows). The proximal displacement of rack 310A proximally displaces gearwheel 312A along track 330. When located proximally along track 330, the teeth of gearwheel 312A are disengaged from gearwheel 312B. Any additional proximal displacement of rack 310A rotates gearwheel 312A in a free manner (shown by arrow), without synchronized motion of gearwheel 312B. Advantageously, the injection syringe may be loaded while attached to the device without causing a synchronized corresponding displacement of the plunger of the aspiration syringe.

FIG. 3B illustrates distal displacement of plunger 306A of injection syringe 304A, for example, to prepare for injection of fluid 340, or during injection of fluid 340 and corresponding aspiration of fluid 342. The distal displacement of rack 310A distally displaces gearwheel 312A along track 330. The distal displacement of gearwheel 312A re-engages gearwheel 312A with gearwheel 312B. Any additional distal displacement of rack 310A rotates gearwheel 312A with synchronized motion of gearwheel 312B and resulting aspiration into syringe 304B, as described hereinabove (shown by arrows).

Figure 4:
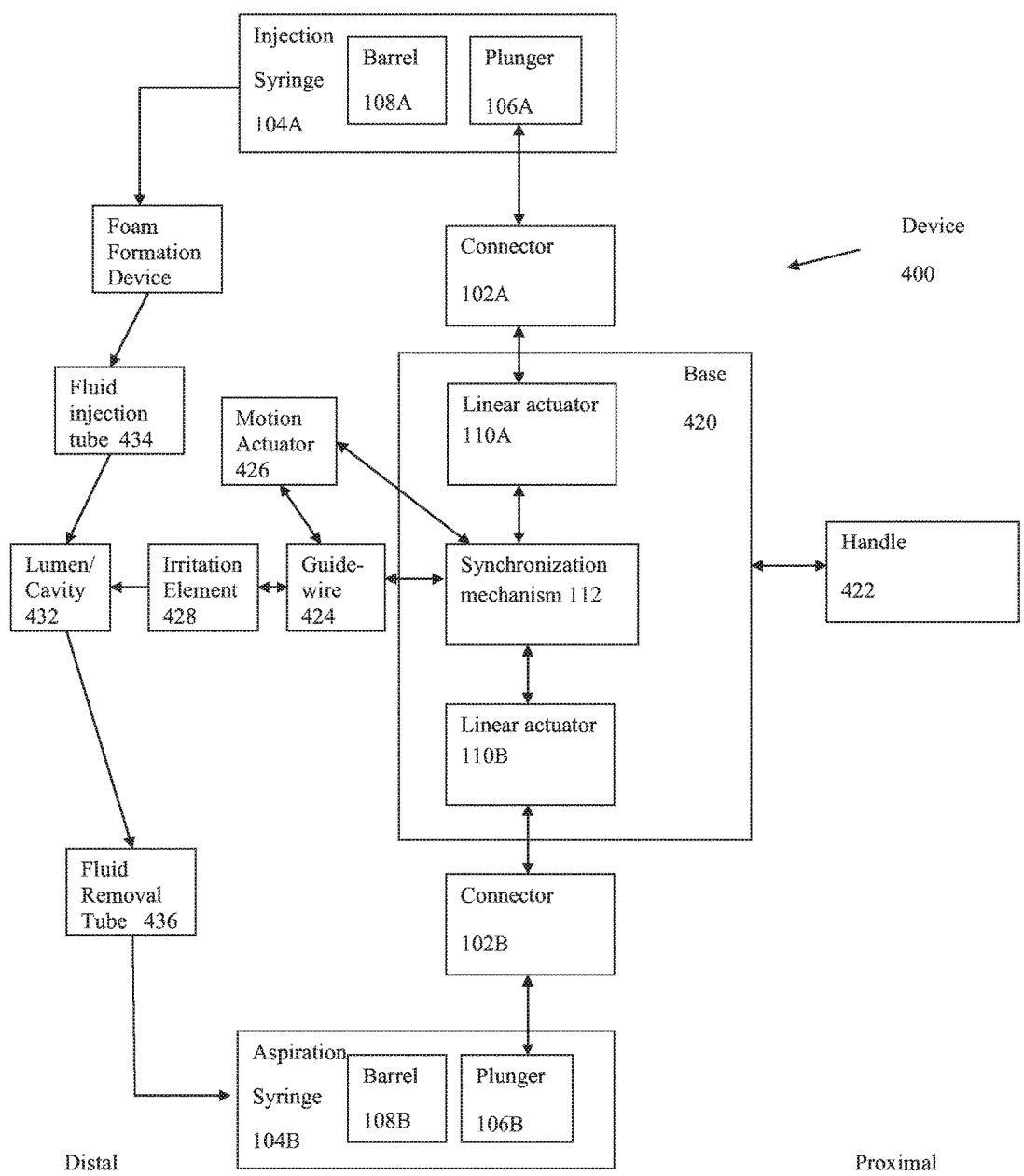
FIG. 4 is the block diagram of a system for synchronized injection and aspiration, showing additional optional features to the device of FIG. 1, in accordance with some embodiments of the present invention.

Reference is now made to FIG. 4, which is a block diagram of a system 400 for synchronized injection and aspiration, showing additional optional features of device 100 of FIG. 1, in accordance with exemplary embodiments of the present invention.

Optionally, device 400 comprises a base 420 for support of synchronization mechanism 112 and/or linear actuators 110A-B, for example, as described with reference to base 220 of FIG. 2.

Optionally, device 400 comprises a handle 422, optionally sized for being held in the palm of one hand. Optionally, handle 422 is foldable. Optionally, base 420 is formed in the shape of handle 422. Alternatively, handle 422 extends outwards from base 420.

Optionally, a proximal end portion of a guidewire 424 is coupled to device 400 so that guidewire 424 is moved during injection and/or aspiration. Optionally, guidewire 424 is coupled to synchronization mechanism 112. Optionally, guidewire 424 is coupled to a gear of mechanism 112, for example, to gearwheel 212C, as illustrated in more detail in reference to FIG. 5A.

During injection and/or aspiration, guidewire 424 is moved by mechanism 112. An optional motion actuator 426 translates at least some of the energy from the motion of the guidewire by mechanism 112 into one or other types of motion. For example, distal and/or proximal linear motion is translated into rotational and/or lateral motion. Additional details are provided with reference to FIGS. 5A-D.

Optionally, guidewire 424 is sized for insertion into a body of a patient, for example, into a blood vessel and/or body chamber.

Optionally, the distal end portion of guidewire 424 is attached to an irritation element 428 sized and arranged to contact at least a portion of an internal wall (e.g. intima tissue layer) of a blood vessel (e.g. vein) or cavity. Irritation of the inner wall may help ablate the blood vessel by increasing the penetration of a drug in the vessel lumen into the vessel wall. Irritation element 428 irritates the inner wall by being moved, the movement transmitted by guidewire 424 from mechanism 112. Examples of irritation elements 428 are described, for example, in co-filed Application with Attorney Docket No. 59920, and for example, in International Patent Application Publication No. WO 2009/109967, both by the same inventor as the present application.

Optionally, injection syringe 104A is in fluid communication with a foam formation device 430 for producing at least some foam from the fluid in injection syringe 104A. The foam is produced after the fluid is ejected from syringe 104A, so that the foam is directly injected into the patient. Examples of foam formation devices 430 are described in more detail, for example in the Application with Attorney Docket No. 59919.

One example of a set-up for device 400 is for treatment of a lumen and/or cavity 432 of a patient. Optionally, injection syringe 104A is placed in fluid communication with lumen 432 by a fluid injection tube 434, for example, a clear disposable sterile tube, such as those used in medical procedures. The proximal end of tube 434 is attached to syringe 104A, for example, to the luer tip thereof. The distal end of tube 434 is attached to a connection inside lumen 432, for example, a catheter. A fluid removal tube 436 provides fluid communication between lumen 432 and aspiration syringe 104B, for example, through the catheter. Optionally, guidewire 424 with irritation element 428 is disposed in lumen 432.

Figure 5A:
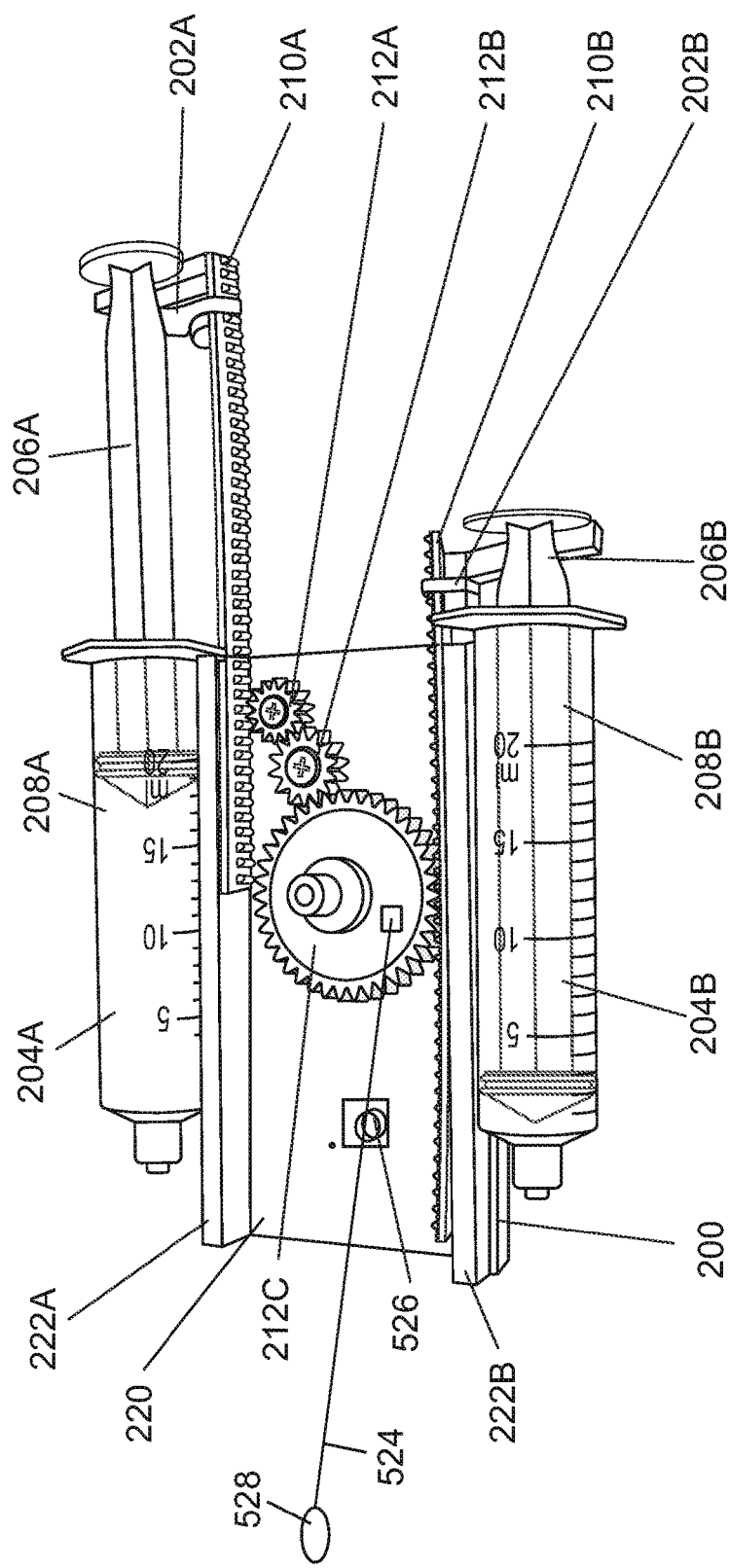
FIG. 5A in an image.

Reference is now made to FIG. 5A, which is a schematic of a guidewire 524 with optional irritation element 528, coupled to the synchronizing mechanism of device 200 of FIG. 2, in accordance with exemplary embodiments of the invention. Advantageously, an inner wall of a lumen or cavity may be irritated in a synchronized manner with fluid injection and aspiration, for example, for vein ablation.

Optionally, guidewire 524 is coupled to the surface of gearwheel 212C. Rotating gearwheel 212C distally or proximally displaces guidewire 524, with some possible rotation and/or lateral movement. Alternatively, guidewire 524 is coupled to other gearwheels, or to other dedicated gears that move during use (not shown). Guidewire 524 may be attached, for example, by a bearing allowing the guidewire to remain relatively straight relative to the moving gear, or by crimping, clamping, friction tight fit, glue, weld, or other connections. Optionally, guidewire 524 is reversibly attached so that guidewire 524 is removable and/or replaceable.

Optionally, guidewire 524 is coupled to an outer perimeter region of gearwheel 212C. Optionally guidewire 524 is wound around the central axis of gearwheel 212C during injection. Advantageously, the guidewire is retracted as the length of the guidewire is shortened by being wound around the axis during injection. Advantageously, the guidewire may be removed out of the lumen or cavity in this manner. Alternatively, guidewire 524 does not wind around the central axis of gearwheel 212C, but is free to move in a distal and proximal direction as the gearwheel turns. Optionally, the distance of displacement is selectable by the location of the coupling of guidewire 524 to gearwheel 212C. Positions relatively further away from the central axis (i.e. towards the outer perimeter) will cause relatively larger displacements. Advantageously, the guidewire does not continuously retract and shorten, but may be maintained at a relatively constant position in the vein.

Optionally, guidewire 524 passes through an elevation with a channel 526 on base 220. Optionally, channel 526 confines motion of guidewire 524 to distal and/or proximal displacement, for example, channel 526 is relatively long and/or narrow.

Optionally, channel 526 serves as motion actuator 426 (of FIG. 4), translating proximal and/or distal displacement into other types of motion, as described below with reference to FIGS. 5B-5D.

Figures 5B, 5C, 5D:
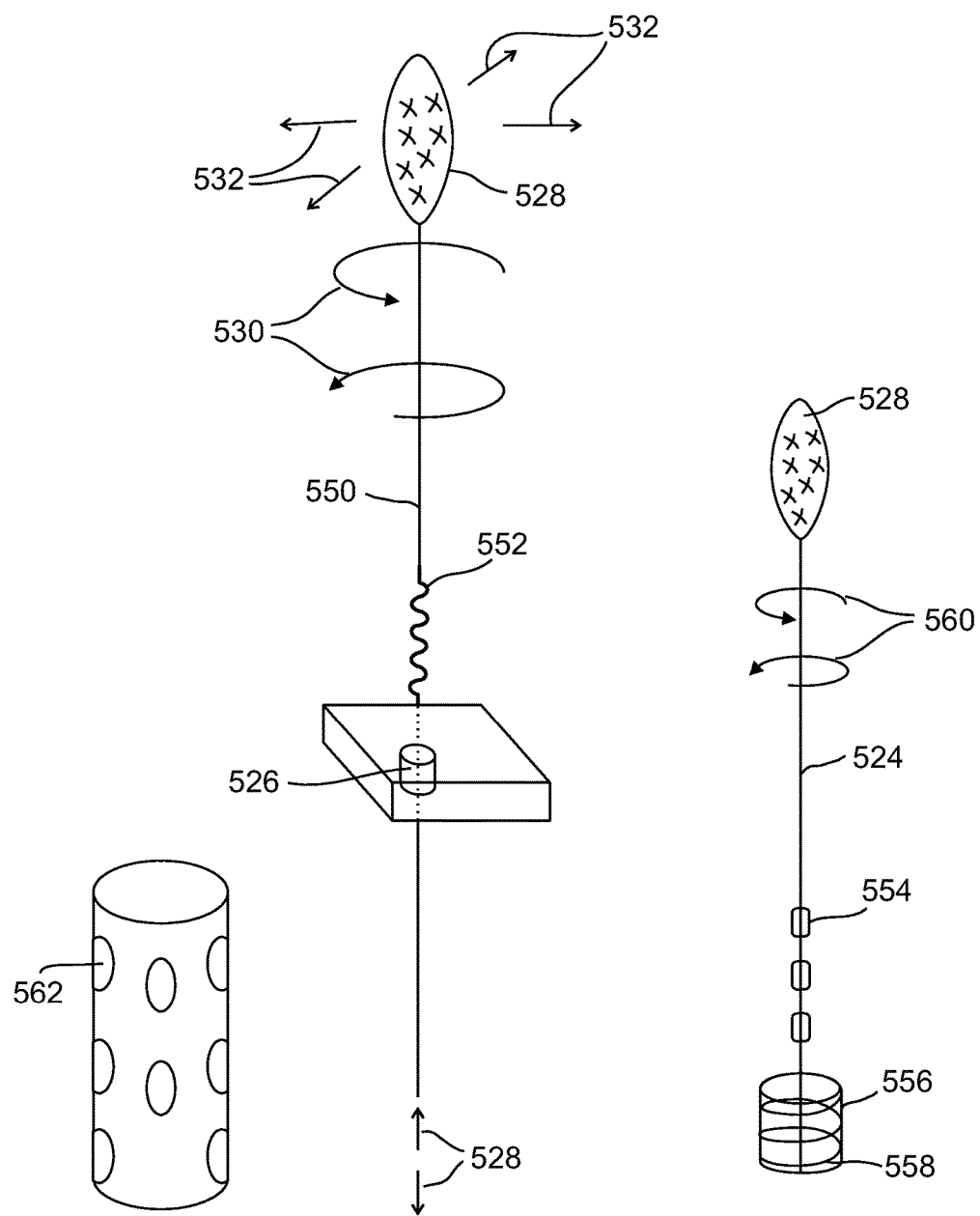
FIGS. 5B-D are schematic illustration of embodiments for coupling the guidewire to the device, in accordance with some embodiments of the present invention.

FIG. 5B is a schematic of a guidewire 550 with optional irritation element 528 at a distal end thereof. Guidewire 550 passes through channel 526.

Guidewire 550 comprises a plurality of features 552 sized and positioned to interact with channel 526 during distal and/or proximal displacement of guidewire 550 through channel 526. The features are, for example, guidewire twisted into a pattern at a portion thereof (e.g. sinusoid, helix), particles attached to guidewire 550 (e.g. boxes, spheres), or other suitable features. The interaction of features 552 with channel 526 translates energy from distal or proximal displacement (represented by arrows 528) of guidewire 550 by the synchronization mechanism into rotational motion (represented by arrows 530) and/or lateral motion (arrows 532).

FIG. 5C is a schematic of guidewire 524 with features 554 (e.g. boxes attached at a portion thereof) passing through a channel 556 having surface features 558 at least on a portion of an internal surface thereof. Optionally, guidewire features 554 interact with channel surface features 558 as guidewire 524 is displaced through channel 556.

Optionally, surface features are designed to produce a desired motion of guidewire 524. For example, the helical surface feature 558 shown may actuate proximal and/or distal energy of displacement of guidewire 524 through channel into rotational motion of guidewire 524 (represented by arrows 560).

FIG. 5D is another example of surface features of the channel for interacting with the guidewire and/or with the guidewire features, a plurality of spaced apart elevations 562, for example, half-spheres.

Figure 6:
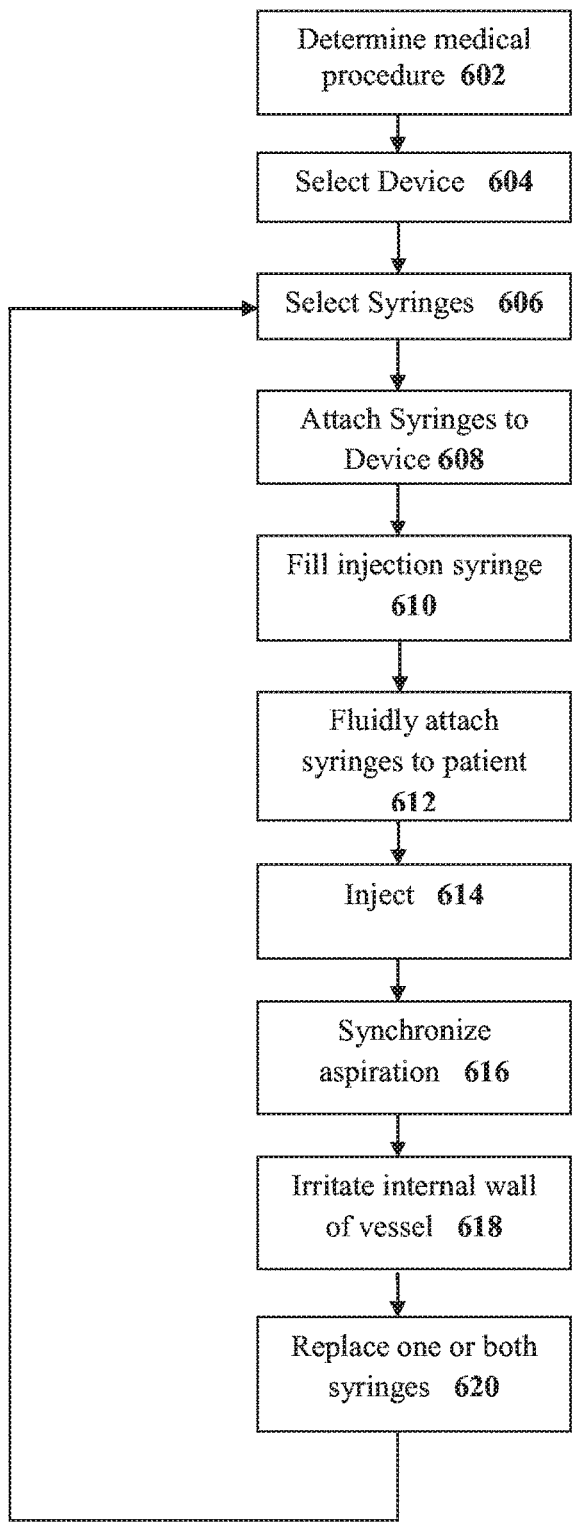
FIG. 6 is a flowchart of a method of use of a synchronization device, in accordance with exemplary embodiments of the present invention.

Reference is now made to FIG. 6, which is a flowchart of a method of operation and/or use of a device for synchronized injection and aspiration (e.g. as described herein), in accordance with exemplary embodiments of the present invention.

Optionally, at 602, the medical procedure suitable for treatment using the device is determined. Indications of suitability of the procedure include, for example: the need for simultaneous injection and removal of fluids, the need for maintaining pressure within a cavity (substantially equal insertion and removal of fluid maintains the pressure within a cavity relatively constant), the need to quickly remove harmful drugs from the body after local action.

Examples of procedures include: draining and flushing-out of an abscess, injection of therapeutics into a body cavity that needs to be maintained at a constant pressure (e.g. joint space), injection of sclerosing agents for vein ablation and removal of the agent to prevent the agent from reaching circulation.

Optionally, at 604, the synchronization device is selected. Optionally, the synchronization device is selected to have a predetermined ratio between proximal displacement and corresponding distal displacement, for example, as described with reference to FIG. 1.

Optionally, at 606, the syringes are selected. Optionally, the volume of the syringes is selected according to the selected device of box 604 and/or according to the procedure of box 602. For example, if the ratio is 1:1, two syringes of equal sizes may be selected. In another example, if several different syringes with different drugs are used to inject, small syringes (e.g. 10 milliliters (mL)) may be used for injection, and one large syringe may be used to collect all the fluid (e.g. 60 mL). The device may be selected to have equal volume changes between 10 mL and 60 mL syringes according to the plunger displacement distances. The 60 mL plunger may require less displacement than the 10 mL plunger to obtain the same change in volume.

In another example, the syringes and/or device may be selected according to the injection pressure and/or the suction pressure they may produce under standard use (e.g. using fingers to apply the force). For example, to prevent using a syringe capable of generating high suction pressure under normal use (which may cause damage by suctioning tissue), a device with a connector unable to connect to the high suction syringe may be selected.

Optionally, at 608, the syringes are connected to the device, for example, by clicking the syringes into the connectors.

Optionally, at 610, the plunger of the injection syringe is retracted to aspirate the fluid for injection into the injection syringe. Optionally, the retraction of the plunger detaches the actuator from the synchronization mechanism so that the syringe is filled without affecting the aspiration syringe. Alternatively, the syringe is first filled and then attached to the device.

Optionally, at 612, the syringes are placed in fluid communication with the anatomical area of the patient being treated. For example, the syringes are connected to tubes and/or to a catheter positioned within the patient.

Optionally, a guidewire with an irritation element at distal end thereof is inserted into the vein.

At 614, fluid is inserted into the patient. Optionally, the plunger of the injection syringe is depressed, for example, manually by a finger of a user, and/or automatically, by a computer controlling a lever.

At 616, fluid is removed from the patient. The device automatically retracts the plunger of the aspiration syringe in synchronization with the injection, so that fluid is aspirated into the aspiration syringe.

Optionally, at 618, the internal wall of vein is automatically irritated during the fluid insertion and aspiration.

At 620, one or both syringes are replaced independently of one another. Optionally, one or both syringes are replaced during the procedure itself. For example, the first inspiration syringe is replaced with another syringe to inject another drug, or a filled aspiration syringe is replaced with a new empty syringe. Alternatively, the syringes are removed and the device is cleaned and ready to be loaded with new syringes, ready for the next procedure.

Figure 7A:
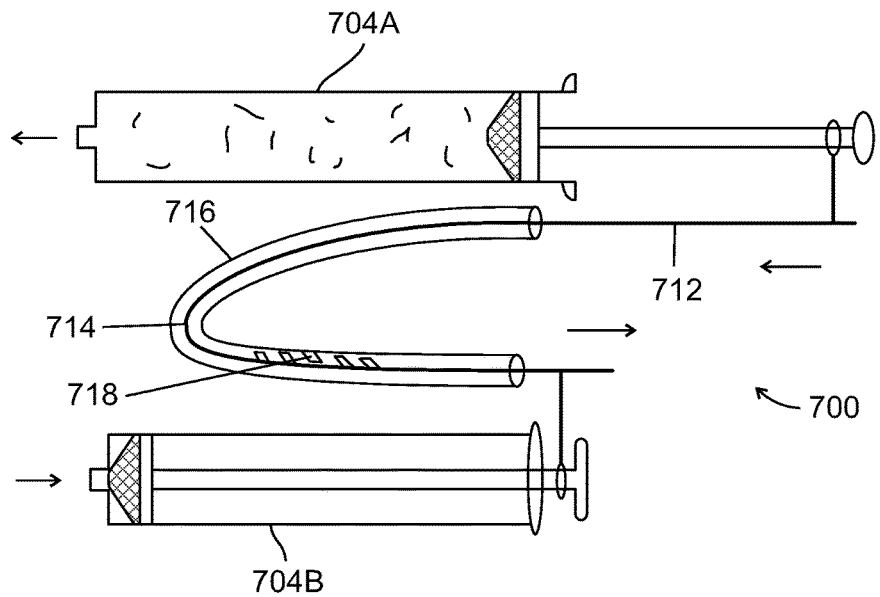
FIGS. 7A-B are schematic illustrations of other embodiments of the synchronization mechanism of the syringe synchronization device, in accordance with exemplary embodiments of the present invention.

Reference is now made to FIG. 7A, which is another embodiment of a synchronization mechanism 700 for a device for synchronized injection and aspiration, in accordance with exemplary embodiments of the present invention.

Mechanism 700 comprises of a rigid and flexible rod 712 that does not buckle under applied forces experienced by the device during use. Rod 712 is made, for example, from metal, plastic or other suitable materials.

One end portion of rod 712 is coupled to the end portion of a plunger of an injection syringe 704A. The other end portion of rod 712 is coupled to the end portion of a plunger of an aspiration syringe 704B.

Rod 712 connects the two plungers through a distally disposed curve portion 714. Curve portion 714 of rod 712 is surrounded by a tube 716 that is held stationary relative to the syringes, for example, tube 716 is attached to a base. The internal diameter of tube 716 is larger than the outer diameter of rod 712 so that rod 712 is able to slide and displace inside tube 716.

In use, injection using syringe 704 distally displaces the attached end of rod 712 and proximally displaces the other end of rod 712. The other end of rod 712, being attached to the plunger of aspiration syringe 704B, distally displaces the plunger thereof.

Optionally, a ratchet mechanism 718 allows only for one-way motion during use, for example, only injection by syringe 704A and aspiration by syringe 704B. Attempt at the opposite action (aspiration by syringe 704A and injection by syringe 704B) is opposed by ratchet 718. After a first use, in order to prepare rod 712 for subsequent uses, rod 712 may be disconnected from the plungers, pulled entirely through tube 716 and out of ratchet 718, and partially re-inserted back into tube 716 and ratchet 718.

Figure 7B:
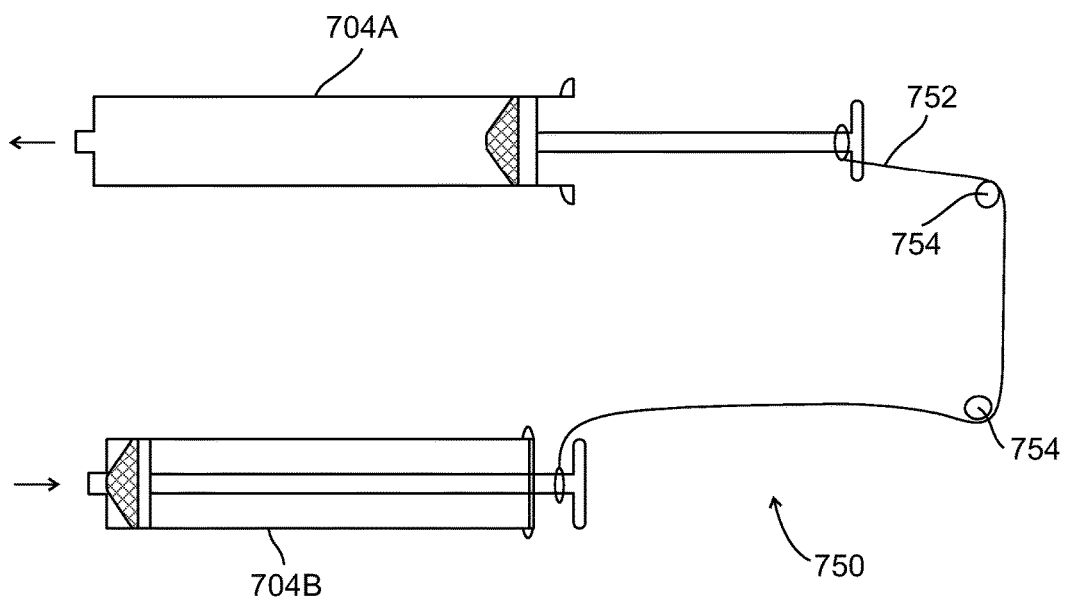

Reference is now made to FIG. 7B, which is another embodiment of a pulley system 750 synchronization mechanism for a device for synchronized injection and aspiration, in accordance with exemplary embodiments of the present invention.

Pulley system 750 comprises a wire 752 with one end attached to the plunger of injection syringe 704A and the other end attached to the plunger of aspiration syringe 704B. Wire 752 winds around one or more pulleys 754.

Optionally, pulley 750 is mostly located proximally relative to injection syringe 704A and aspiration syringe 704B. Alternatively, pulley 750 is located mostly distally. Alternatively, pulley 750 is distributed both proximally and distally.

Optionally, for the devices of both FIGS. 7A and 7B, linear actuators are used, so that ends of the rod and/or wire are attached to the linear actuators (which are coupled to the plungers) instead of being directly connected to the plungers.

It is expected that during the life of a patent maturing from this application many relevant syringe synchronization actuators will be developed and the scope of the term syringe synchronization actuator is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for automatic synchronized injection and aspiration of fluids comprising:
    a first linear actuator,
    a second linear actuator;
    a first coupling mechanism attached at a distal end portion of the first linear actuator, the first coupling mechanism arranged for detachable coupling to a first plunger of a first syringe;
    a second coupling mechanism attached at a distal end portion of the second linear actuator, the second coupling mechanism arranged for detachable coupling to a second plunger of a second syringe; and
    a synchronization mechanism mechanically coupled to the first and second linear actuators, the synchronization mechanism arranged so that insertion of the first plunger further into a first barrel of the first syringe is synchronized with extraction of the second plunger from a second barrel of the second syringe, thereby injection from the first syringe is synchronized with aspiration into the second syringe;
    wherein the mechanical coupling of the synchronization mechanism to the first and second linear actuators includes a disengaging mechanism comprising a track configured to one or more of (i) permit the first linear actuator to releasably slide along or parallel to the track out of engagement with the synchronization mechanism when the first plunger is pulled out of the first barrel or (ii) permit the second linear actuator to releasably slide along or parallel to the track out of engagement with the synchronization mechanism when the second plunger is pulled out of the second barrel.

2. The device of claim 1, wherein the first linear actuator is coupled to a first gear of the synchronization mechanism, the first gear being mounted on the track substantially parallel to a direction of movement of the first linear actuator, so that proximal displacement of the first linear actuator disengages the first gear from the rest of the synchronization mechanism and distal displacement of the first linear actuator re-engages the first gear with the rest of the synchronization mechanism.

3. The device of claim 1, wherein the synchronization mechanism has 3 gearwheels which synchronize opposite movements of the first and second linear actuators.

4. The device of claim 1, wherein the synchronization mechanism has a rigid and flexible rod with a curve, one end of the rigid and flexible rod being coupled to the first linear actuator and an other end of the rigid and flexible rod being coupled to the second linear actuator so that opposite movements of the first and second linear actuator are synchronized.

5. The device of claim 1, wherein the synchronization mechanism has a wire winding around one or more pulley, one end of the wire being coupled to the first linear actuator, an other end of the wire being coupled to the second linear actuator, so that opposite movements of the first and second linear actuator are synchronized.

6. The device of claim 1, wherein the first and second linear actuators have teeth, and the synchronization mechanism comprises a plurality of meshed gears, wherein at least a first gear is meshed with the teeth of the first linear actuator and at least a second gear is meshed with teeth of the second linear actuator.

7. The device of claim 1, wherein the synchronization mechanism is arranged so that distal displacement of the first linear actuator by a first distance is synchronized with proximal displacement of the second linear actuator by a second distance substantially different than the first distance.

8. The device of claim 7, wherein a ratio between the second and the first distance corresponds to equal volume changes in the first and second syringes, wherein volume capacities of the first and second syringes are different.

9. The device of claim 1, further comprising a base, the synchronization mechanism being mechanically attached to the base, the base comprising barrel attachment elements for reversibly coupling the barrels of the syringes to the base in a stable and substantially motion-less manner.

10. The device of claim 1, wherein the first and second syringes are disposable syringes.

11. The device of claim 1, wherein the first and second syringes are of different volume capacities.

12. The device of claim 1, wherein the first and second linear actuators are racks.

13. The device of claim 1, further comprising a guidewire having a proximal end portion coupled to the synchronization mechanism so that the guidewire is displaced one or both of distally and proximally during distal displacement of the first linear actuator.

14. The device of claim 13, wherein a distal end portion of the guidewire comprises an irritation element sized and arranged to contact at least a portion of an internal wall of a vessel or cavity so that the displacement of the guidewire is configured to irritate the internal wall of the vessel or cavity.

15. The device of claim 13, wherein the guidewire is coupled to the synchronization mechanism so that the guidewire is proximally retracted during injection.

16. The device of claim 15, wherein the guidewire is attached to an outer perimeter portion of a gear of the synchronization mechanism so that the guidewire is wound around an axle of the gear during injection, thereby retracting the guidewire.

17. The device of claim 13, further comprising a channel for at least partially surrounding a portion of the guidewire, the guidewire arranged with one or more features at the portion of the guidewire so that displacement of the portion of the guidewire through the channel one or both of rotates and laterally displaces the guidewire.

18. The device of claim 17, wherein the internal surface of the channel comprises one or more surface features so that passage of the guidewire portion features through the channel one or both of rotates and laterally displaces the guidewire.

19. A method of synchronized injection and aspiration of fluids comprising:

selecting a first syringe suitable for injection of a first fluid;

selecting a second syringe suitable for aspiration of a second fluid;

detachably attaching the first and second syringes to a synchronization mechanism;

using a synchronization mechanism for synchronizing a distal displacement of a first plunger of the first syringe with a proximal displacement of a second plunger of the second syringe using a mechanical synchronization arrangement having a plurality of linear actuators so that injection by the distal displacement and aspiration by the proximal displacement occur simultaneously;

disengaging one of the plurality of linear actuators from the synchronization mechanism by releasably sliding one of the plurality of linear actuators along or parallel to a track relative to the synchronization mechanism when a plunger coupled to one of the plurality of linear actuators is pulled out of a corresponding barrel of one of the first syringe and the second syringe; and replacing one of the first or second syringe with a third syringe, wherein the replacing is performed independently of the other of the first or second syringe.

20. The device of claim 1, wherein said synchronization mechanism comprises a first gearwheel and a second gearwheel, said second gearwheel is mounted within a track and engaged with a rack of said first linear actuator;

wherein said second gearwheel moves proximally and distally in a direction substantially parallel to a direction of movement of said rack and said first linear actuator for engaging and disengaging with said first gearwheel.

* * * * *